United States Patent [19]

Horoschak et al.

[11] Patent Number: 5,314,684
[45] Date of Patent: May 24, 1994

[54] WATER-BASED FIXATIVE COMPOSITION

[75] Inventors: John R. Horoschak, Hamden; Paul S. Wallace, Cos Cob, both of Conn.

[73] Assignee: Clairol Inc., New York, N.Y.

[21] Appl. No.: 964,580

[22] Filed: Oct. 21, 1992

Related U.S. Application Data

[63] Continuation of Ser. No. 735,578, Jul. 25, 1991, abandoned.

[51] Int. Cl.$^5$ ............................................. A61K 7/11
[52] U.S. Cl. .................................. 424/71; 424/78.08; 424/DIG. 1; 424/DIG. 2; 424/47
[58] Field of Search ............... 424/81, 83, 71, DIG. 1, 424/DIG. 2, 47, 45; 524/602

[56] References Cited

U.S. PATENT DOCUMENTS

| | | | |
|---|---|---|---|
| 3,734,874 | 5/1973 | Kibler et al. | 523/455 |
| 4,335,220 | 6/1982 | Coney | 524/602 |
| 4,733,677 | 3/1988 | Gee et al. | 424/71 |
| 4,871,529 | 10/1989 | Sramek | 424/71 |
| 4,950,475 | 8/1990 | Vishnupad et al. | 424/83 |
| 5,053,221 | 10/1991 | Robertson et al. | 424/81 |
| 5,085,859 | 2/1992 | Halloran et al. | 424/71 |
| 5,104,642 | 4/1992 | Wells et al. | 424/47 |
| 5,158,762 | 10/1992 | Pierce | 424/47 |

FOREIGN PATENT DOCUMENTS 56-166109 12/1981 Japan .

Primary Examiner—Thurman K. Page
Assistant Examiner—Raj Bawa
Attorney, Agent, or Firm—Morton S. Simon

[57] ABSTRACT

The hair fixative composition contains from about 2 to about 10 weight %, based on the weight of the composition, of a water-dispersible amorphous thermoplastic hair fixative polyester whose polymer chain is represented by the structure:

$$\text{HO}-\text{G}-\text{A}-\text{G}-\text{A}-\text{G}-\text{A}-\text{G}-\text{A}-\text{G}-\text{A}-\text{G}-\text{OH}$$
$$| \qquad\qquad\qquad\qquad |$$
$$\text{SO}_3^-\text{Na}^+ \qquad\qquad \text{SO}_3^-\text{Na}^+$$

wherein A is an aromatic dicarboxylic acid moiety, G is an aliphatic or cycloaliphatic glycol residue, on the average there being 5 to 8 sodiosulfo substituents per molecule. The fixative polyester is in colloidal suspension in the composition. The composition further contains from about 0.1 to about 3 weight %, based on the weight of the composition, of a copolymer containing dimethylpolysiloxane and organo-modified methylsiloxane moieties. Such amount is sufficient to cause the composition to spread out on a hair shaft when the composition is applied to same. The composition also contains from 0 to about 25 weight %, based on the weight of the composition, of a lower alcohol and sufficient water to bring the composition to 100 weight %. When sprayed on the hair, the composition has a wetness perception comparable to that of compositions containing high concentrations of lower alcohol.

25 Claims, No Drawings

WATER-BASED FIXATIVE COMPOSITION

This is a continuation of application Ser. No. 735,578, filed Jul. 25, 1991, entitled Water-Based Fixative Composition and now abandoned.

FIELD OF INVENTION

The present invention relates to water-based hair spray compositions which incorporate a hair fixative polymer. More specifically, the present invention relates to such compositions containing reduced amounts of lower alkanol to no lower alkanol.

BACKGROUND OF INVENTION

Typical prior art hair spray compositions employ polymeric fixatives to hold the hair set. They also contain large amounts of lower alkanol in order to solubilize the polymer fixative. As used herein, lower alkanol means $C_1$ to $C_5$ alkanols such as ethanol and isopropanol. The lower alkanol additionally serves as primary solvent for the formulation. The lower alkanol content of prior art compositions makes compositions known in the art flammable. Their flammability presents obvious dangers in the manufacture of such formulations and in their use by end users. Moreover, there is a wide spread perception, among such end users, that the lower alkanol in products intended for application to hair is harmful to the hair. Moreover, increased environmental awareness, of both government and consumers, has led to increased effort on the part of manufacturers to decrease the amount of volatile organic compounds in their hair care products, particularly hairsprays. Lower alkanols are the primary volatile organic compounds contained in hair spray products. Consequently, the desirability of formulating a hair fixative product which contains small amounts of lower alkanol to, preferably, no lower alkanol, and which can be utilized in a pumpable delivery system, is self-evident. Despite the fact that a pumpable hair fixative product containing little or no lower alkanol, in other words, a product which is substantially water based, would be desirable from a marketing perspective, no such pumpable product has as yet been successfully commercialized. The state of the art does not permit the development of a water-based fixative hair composition which performs similarly to conventional lower alkanol/polymeric systems. Attempts to replace lower alkanol with water, in conventional systems, have resulted either in only partially substituted systems, due to the solubility limits of conventional hair fixative polymers in water, or, in fully substituted formulations which when delivered from conventional pump sprayers, dispense and perform unacceptably. These formulas, which use water as the primary solvent, tend to dispense a large particle spray, have a very long drying time, and give the treated hair an unnatural look.

The present invention provides compositions which resolve the aforementioned deficiencies of prior art compositions. The compositions of the instant invention contain a polymer which serves as a hair fixative. The hair fixative polymer is water dispersible and forms a continuous film on the hair shaft.

The present inventors have found that the key to providing an acceptable dispensing pattern and acceptable hair spray characteristics, is inclusion, in the compositions of the invention, of a copolymer containing dimethyl polysiloxane and organo-modified methylsiloxane moieties. Such copolymer is hereinafter referred to by the CFTA name, dimethicone copolyol. Surprisingly, the addition of this material produces an unexpected improvement in the reduction of wetness perception. It is believed that this material provides the perceived performance benefit partly by reducing the surface tension of the composition. This allows for the dispensing of smaller, more uniform, droplets. Moreover, due to the surfactant properties of the dimethicone copolyol, a more uniform coating of resin on the hair shaft is quickly obtained. This is evidenced by a dramatic reduction of clumping and matting of the hair. It may well be that the surfactant/conditioning properties of this particular dimethicone copolyol causes the compositions of the present invention to spread out and penetrate the hair shaft more rapidly.

In essence, the present invention resides in the novel use of dimethicone copolyol to enhance the performance of water-based hair spray formulations containing polymeric hair fixatives.

The dimethicone copolyol utilizable in the instant invention is available from Union Carbide, under the tradenames SILWET L-7614, SILWET L-7600, and SILWET L-7604. It is also available from DOW CORNING under the tradenames Silicone 190 Surfactant and Silicone 193 Surfactant.

The polyester polymers found to be of utility in the practice of the present invention are water-dissipatable polymers such as disclosed in U.S. Pat. No. 4,335,220 to Coney entitled "Sequestering Agents and Compositions Produced Therefrom." According to the Coney patent, certain polymeric polyesters that comprise the reaction products of (a) at least one difunctional dicarboxylic acid; (b) at least one difunctional sulfomonomer containing at least one metal sulfonate group attached to an aromatic nucleus, the functional groups being hydroxy, carboxyl or amino, and (c) a glycol or a glycol and diamine mixture, the diamine having two —NRH groups and the glycol containing two —CH$_2$OH groups of which at least 0.1 mole percent, based on the total mole percent of hydroxy or hydroxy and amino equivalents, is a poly(ethylene glycol) having the structural formula H(OCH$_2$—CH$_2$)n OH, n being an integer of 2 and about 500, with the proviso that the mole percent of the poly(ethylene glycol) within the range is inversely proportional to the quantity of n within the range, said polyester as defined above having an inherent viscosity of at least about 0.1 as defined in the Coney patent and including the reaction products based on the ester forming or esteramide derivatives of said reactants (a), (b), and (c), are suitable to sequester finely divided water insoluble, hydrophobic deformable organic substances of low dipole moment, i.e. from 0 to 18. Examples of such substances are recited by Coney at column 6, lines 12-21 and include sucrose esters, aromatic organic compounds, aliphatic or alicyclic organic compounds, paraffins, vegetable oils, etc. The Coney patent is incorporated herein by reference.

U.S. Pat. Nos. 3,779,993 to Kibler et al; 3,734,874 to Kibler et al and 4,233,196 to Sublett also each relate to compositions comprising an aqueous dissipation of polymers described as linear, water dissipatable, meltable polyesters or polyester-amides prepared from the reaction of glycol, dicarboxylic acid, and difunctional monomer components. Each of these patents discloses that the difunctional sulfomonomer component of the polyesters or polyesteramides therein disclosed may advantageously be a dicarboxylic acid or ester thereof containing a metal sulfonate group, a glycol containing a metal sulfonate group or a hydroxy acid containing a metal sulfonate group, the metal ion of the sulfonate salt being Na+, Li+, Mg+, Ca++, Cu++, Ni++, Fe++, Fe+++ or the like.

Polymeric hair fixatives utilizable in the compositions of the present invention are those that are water dispersible. Particularly preferred are the Eastman AQ polymers. Of these, Eastman polymer AQ-55 is most preferred.

The Eastman AQ polymers are amorphous thermoplastic polyesters inherently dispersible in water. Such materials form hard, clear films without the need for solvents. More specifically, Eastman AQ Polymers are relatively high molecular weight, amorphous polyesters that disperse directly in water without the assistance of organic co-solvents, surfactants or amines. The water dispersibility is attributable to the presence of sodiosulfo ($SO_3{-}Na^+$) substituents in the structure. The polymer chain is represented by the structure:

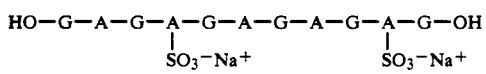

A = an aromatic dicarboxylic acid moiety
G = an aliphatic or cycloaliphatic glycol residue
—OH = hydroxy end groups Some of the aromatic dicarboxylic acid units in Eastman AQ Polymer chains have sodiosulfo ($SO_3{-}Na^+$) substituents. Although only two are shown in the structure set forth above, on the average, there are 5 to 8 ionic sodiosulfo substituents per molecule.

Dimethicone copolyol is an essential component of the present composition. As stated heretofore, it is available from Union Carbide. The Union Carbide SILWET surfactants are copolymers containing dimethylpolysiloxane and organo-modified methylsiloxane moieties. Unlike dimethicone, dimethicone copolyols are soluble in alcohol and soluble in, or readily miscible with, water. The preferred SILWET surfactant is SILWET L-7604. This material is of the type referred to by Union Carbide as alkyl pendant (non hydrolyzable). The pendant polyether is disclosed to be entirely ethyleneoxide. Moreover, it is methoxy terminated. Its weight is disclosed to be 3000 with a copolymer disclosed as 100. SILWET surfactant L-7604 is delineated as having the chemical name organo-modified polymethylsiloxane and as being a member of the organo silicone fluid chemical family.

The compositions of the present invention can contain other ingredients such as, for example, other polymers (e.g. PVP; PVP/VA) preservatives, ingredients to modify pH, fragrance, etc. Suitable preservatives include any and all preservatives commonly employed in cosmetically-acceptable formulations; for example, methylparaben, 2-phenoxyethanol, DMDMH, etc. If it is desired to adjust pH, a material such as aminomethylpropanol may be utilized. Other pH adjusting materials will be self-evident to one skilled in the art.

Although it is not essential, one can include in the formulations of the present invention, co-surfactants which are both oil and water miscible and/or co-solvents, such as glycerin, sorbitol and glycol ethers. The co-surfactants and co-solvents serve to improve the properties of the composition by aiding in solubilization, possibly by a bridge solvent effect. A co-surfactant that is particularly desirable is glycereth-7-triacetate. Co-solvents that are particularly desirable are glycerin, sorbitol, and propylene glycol.

The composition may contain other water soluble polymers as co-fixatives. Such materials are well known to those skilled in the art. They include, for example, polyvinylpyrrolidone, PVP/VA (65/35) and PVP/Dimethylaminoethyl-methylmethacrylate copolymer. Polyvinylpyrrolidone is preferred.

It should be noted that as used herein, all percentages are percent by weight and are based on the total weight of the composition.

The AQ polymer is preferably employed in the compositions of the instant invention, in an amount from about 2% to about 10%. More preferably, it is employed in an amount from about 4% to about 8%. Most preferably, it is employed in an amount of from about 5% to about 7%.

The modified dimethicone copolyol is preferably employed in an amount from about 0.1% to about 3%. More preferably, it is employed in an amount of from about 0.2% to about 2%. Most preferably, it is employed in an amount of from about 0.3% to about 1.0%.

The co-surfactant, when present, is employed in an amount of up to about 5%. More preferably, it is present in a range of from about 0.2% to about 3%. Most preferably, it is present in a range of from about 0.3% to about 1.5%.

The co-solvent, when present, is employed in an amount up to about 5%. More preferably, it is present in an amount of from about 0.2% to about 3%. Most preferably, it is present in an amount of from about 0.3% to about 1.5%.

The co-fixative, when present, is employed in an amount up to about 5%. More preferably, it is present in an amount of from about 0.25% to about 3% and most preferably in an amount of from about 0.5% to about 2%.

Preservative(s), when present, and pH adjusting material(s), when present, are utilized in amounts well known to those skilled in the art and appropriate for the particular material selected.

It is important to note that, although the formulations of the present invention are preferably substantially lower alkanol-free, they may contain from about 0% to about 25% lower alkanol. The presence of lower alkanol s not required, nor does it offer any real advantage. However, it may be desired to employ some lower alkanol in the composition if one wishes to incorporate additional active(s) requiring lower alkanol for solubilization. This may be true for certain sunscreens and other actives. It is the intention of the present inventor to include within the scope of the present invention, other actives, such as vitamins, sunscreens, and the like, which are typically employed in cosmetic formulations intended for application to the hair.

The present invention will now be illustrated with reference to the examples which follow. These examples are intended to illustrate not limit the invention. It is obvious that certain changes can be made without affecting the scope or nature of the invention.

| Material | Examples 1-9 | | | | | | | | |
|---|---|---|---|---|---|---|---|---|---|
| | 1 | 2 | 3 | 4 | 5 | 6 | 7 | 8 | 9 |
| Deionized water | 92.245 | 91.245 | 70.575 | 89.75 | 88.325 | 90.70 | 91.10 | 91.19 | 91.20 |
| Polymer AQ[(1)] | 4.000 | 5.000 | 7.000 | 6.00 | 8.000 | 6.00 | 6.00 | 6.00 | 6.00 |
| Dimethicone copolyol | 1.000 | 1.000 | 1.000 | 1.00 | 0.750 | 0.50 | 0.10 | 0.01 | — |
| Glycereth-7-triacetate | — | — | 0.500 | — | 0.500 | 1.00 | 1.00 | 1.00 | 1.00 |
| Glycerin | 0.300 | 0.300 | 0.300 | 0.30 | 0.300 | 0.30 | 0.30 | 0.30 | 0.30 |
| Polyvinyl pyrrolidone | — | — | 2.000 | — | 1.500 | 1.00 | 1.00 | 1.00 | 1.00 |
| DMDM hydantoin | 0.200 | 0.200 | 0.300 | 0.20 | 0.300 | 0.30 | 0.30 | 0.30 | 0.30 |
| Methylparaben | 0.150 | 0.150 | 0.150 | 0.15 | 0.150 | 0.05 | 0.05 | 0.05 | 0.05 |
| Aminomethyl propanol | — | — | 0.050 | — | 0.050 | 0.05 | 0.05 | 0.05 | 0.05 |
| Fragrance | 0.100 | 0.100 | 0.100 | 0.10 | 0.100 | 0.10 | 0.10 | 0.10 | 0.10 |
| Disodium EDTA | 0.005 | 0.005 | 0.005 | — | 0.005 | — | — | — | — |
| PBP/VA copolymer | 2.000 | 2.000 | — | 2.00 | — | — | — | — | — |
| dl Panthenol | — | — | 0.010 | — | 0.010 | — | — | — | — |
| DEA methoxycinnamate | — | — | 0.010 | — | 0.010 | — | — | — | — |
| Ethanol | — | — | 18.000 | — | — | — | — | — | — |
| Nonoxynol-9 | — | — | — | 0.50 | — | — | — | — | — |
| Surface tension (dynes/cm) | 26.9 | 27.2 | 23.7 | 28.6 | 30.9 | 26.9 | 31.0 | 39.0 | 50.5 |

[(1)]Available from Eastman Chemical Products, Inc. Kingsport, Tenn.

The above compositions were prepared as follows: A suitable container was employed. Eighteen percent of the formulation amount of the water was added to the container then heated to a temperature of 85°–90° C. Under agitation, the methylparaben and AQ polymer were added to the container and the resultant mixture was agitated until uniform. The remainder of the formula amount of water was added and the composition was permitted to cool to 35° C., at which point the remainder of the ingredients were added in the order listed.

The resultant mixture was cooled to a temperature of less than 30° C., at which point the DMDM hydantoin, aminomethylpropanol and fragrance were added.

The resultant mixture was further mixed until uniform. Compositions produced in accordance with Examples 2,4,6,7,8 and 9 were packaged in standard 6 fluid ounce plastic pump containers, provided with a commercially available pump sprayer. The compositions were evaluated in a hair salon. A commercially available hair fixative pump spray product with 88% lower alkanol was utilized for comparative purposes (i.e., CLAIROL's FINAL NET ® hair spray). The salon test demonstrated that under normal application rates the composition of Examples 2,4 and 6 were perceived to dry as rapidly as the commercial product. The salon tests also demonstrated that the composition of Examples 2,4,6,7,8 and 9 performed as well as the comparative commercial product, with regard to hair fixation. It should be noted that the surface tension of Examples 2, 4 and 6 were very close to the FINAL NET ® hair spray control, which is 25 dynes/cm; whereas Examples 8 and 9 have higher surface tensions.

What is claimed is:

1. A hair fixative composition containing
   (i) from about 2 to about 10 weight %, based on the weight of the composition, of a water-dispersible amorphous thermoplastic hair fixative polyester whose polymer chain is represented by the structure

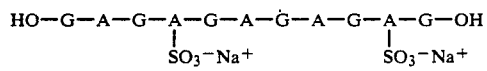

wherein A is an aromatic dicarboxylic acid moiety, G is an aliphatic or cycloaliphatic glycol residue, on the average there being 5 to 8 sodiosulfo substituents per molecule, said fixative polyester being in colloidal suspension in the composition;
   (ii) from about 0.1 to about 3 weight %, based on the weight of the composition, of an amount of copolymer containing dimethylpolysiloxane and organo-modified methylsiloxane moieties, said amount being sufficient to cause the composition to spread out on a hair shaft when the composition is applied to same;
   (iii) from 0 to about 25 weight %, based on the weight of the composition, of a lower alcohol; and
   (iv) sufficient water to bring the composition to 100 weight %.

2. The composition as claimed in claim 1, wherein the polyester polymer has an approximate molecular weight of about 14,000 to about 16,000 and a melt viscosity at 200° C. of about 2,000 to about 42,000 poise as measured with a Seiglaff-McKelvy Capillary Rheometer, 100 sec$^{-1}$ shear rate.

3. The composition as claimed in claim 2, wherein the polyester polymer has an approximate molecular weight, of about 14,000, an hydroxyl number of less than 10, an acid number less than 2, a Tg, 55° C., and a melt viscosity at 200° C. of about 42,000 poise.

4. The composition as claimed in claim 1, wherein the copolymer is a polyalkyleneoxide-modified polydimethylsiloxane block copolymer having the general formula

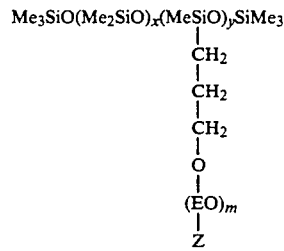

wherein Me is methyl, EO is ethyleneoxy and Z is hydrogen, a molecular weight of about 4000 and an HLB range of 13 to 17.

5. The composition as claimed in claim 1, wherein no lower alcohol is present.

6. The composition according to claim 1, said composition being substantially free of $C_1$ to $C_5$ alkanol.

7. The composition according to claim 1, said composition containing no $C_1$ to $C_5$ alkanol.

8. The composition according to claim 1, said composition containing 0 to 18 weight % of $C_1$ to $C_5$ alkanol.

9. The composition, as claimed in claim 6, wherein the fixative polymer is present in amount of from about 4% to about 8%.

10. The composition, as claimed in claim 6, wherein the fixative polymer is present in amount of from about 5% to about 7%.

11. The composition, as claimed in claim 6, wherein the copolymer is present in an amount of from about 0.2% to about 2%.

12. The composition, as claimed in claim 6, wherein the copolymer is present in an amount of from about 0.3% to about 1.0%.

13. The composition, as claimed in claim 6, further including up to about 5% of a solubilization aiding co-surfactant which is oil and water miscible.

14. The composition as claimed in claim 13, wherein the co-surfactant is present in an amount of from about 0.2% to about 3%.

15. The composition as claimed in claim 13, wherein the co-surfactant is present in an amount of from about 0.3% to about 1.5%.

16. The composition as claimed in any one of claims 13, 14 or 15, wherein the co-surfactant is glycereth-7-triacetate.

17. The composition as claimed in claim 6, further including up to about 5% of a co-solvent to aid in solubilization.

18. The composition, as claimed in claim 17, wherein said co-solvent is present in an amount of from about 0.2% to about 3%,.

19. The composition, as claimed in claim 17, wherein said co-solvent is present in an amount of from about 0.3% to about 1.5%.

20. The composition, as claimed in any one of claims 17, 18 or 19, wherein said co-solvent is selected from the group consisting of glycerin, sorbitol, glycol ethers and mixtures thereof.

21. The composition, as claimed in claim 6, further including up to about 5% of a co-fixative.

22. The composition, as claimed in claim 6, further including from about 0.25% to about 3% of a co-fixative.

23. The composition, as claimed in claim 6, further including from about 0.5% to about 2% of a co-fixative.

24. The composition, as claimed in any one of claims 21, 22 or 23, wherein the co-fixative is selected from the group consisting of polyvinylpyrrolidone, PVP/VA (65/35) and PVP/dimethylaminoethyl-methacrylate copolymer.

25. The composition, as claimed in any one of claims 21, 22 or 23, wherein the co-fixative is polyvinylpyrrolidone.

* * * * *